US00PP33548P2

(12) United States Plant Patent
Wood

(10) Patent No.: US PP33,548 P2
(45) Date of Patent: Oct. 12, 2021

(54) ***CHAMAECYPARIS* PLANT NAMED 'SMNCLUTL'**

(50) Latin Name: *Chamaecyparis lawsoniana*
Varietal Denomination: SMNCLUTL

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 17/039,902

(22) Filed: Sep. 30, 2020

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ... A01H 7/00; A01H 5/04; A01H 5/00; A01H 5/12; A01H 5/02
See application file for complete search history.

*Primary Examiner* — June Hwu
(74) *Attorney, Agent, or Firm* — C. Anne Whealy

(57) ABSTRACT

A new and distinct cultivar of *Chamaecyparis* plant named 'SMNCLUTL', characterized by its upright, arching and uniform plant habit and pyramidal plant form; freely branching habit, dense and bushy plant form; leaves that retain their yellow green coloration; and good garden performance.

1 Drawing Sheet

Botanical designation: *Chamaecyparis lawsoniana.*
Cultivar denomination: 'SMNCLUTL'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present Invention relates to a new and distinct cultivar of *Chamaecyparis* plant, botanically known as *Chamaecyparis lawsoniana*, and hereinafter referred to by the name 'SMNCLUTL'.

The new *Chamaecyparis* plant is a product of a planned breeding program conducted by the Inventor in Grand Haven, Mich. The objective of the breeding program was to create new *Chamaecyparis* plants with strong branches, attractive plant form and good leaf color retention.

The new *Chamaecyparis* plant originated from an open-pollination in 2008 in Grand Haven, Mich. of *Chamaecyparis lawsoniana* 'Sullivan', not patented, as the female, or seed, parent with an unknown proprietary selection of *Chamaecyparis lawsoniana* as the male, or pollen, parent. The new *Chamaecyparis* plant was discovered and selected by the Inventor as a single flowering plant within the progeny of the stated open-pollination in a controlled environment in Grand Haven, Mich. in 2016.

Asexual reproduction of the new *Chamaecyparis* plant by softwood cuttings in a controlled greenhouse environment in Grand Haven, Mich. since 2016 has shown that the unique features of this new *Chamaecyparis* plant are stable and reproduced true to type in successive generations.

SUMMARY OF THE INVENTION

Plants of the new *Chamaecyparis* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of the new *Chamaecyparis* plant. These characteristics in combination distinguish 'SMNCLUTL' as a new and distinct cultivar of *Chamaecyparis* plant:

1. Upright, arching and uniform plant habit and pyramidal plant form.
2. Freely branching habit, dense and bushy plant form.
3. Leaves that retain their yellow green coloration.
4. Good garden performance.

Plants of the new *Chamaecyparis* can be compared to plants of the female parent selection, 'Sullivan'. In side-by-side comparison, plants of the new *Chamaecyparis* differ primarily from plants of 'Sullivan' in the following characteristics:

1. Plants of the new *Chamaecyparis* are broader and more pyramidal in shape than and not as narrow and conical in shape as plants of 'Sullivan'.
2. Leaves of plants of the new *Chamaecyparis* are thread-like in shape whereas leaves of plants of 'Sullivan' are scale-like in shape.

Plants of the new *Chamaecyparis* can also be compared to plants of *Chamaecyparis pisifera* 'Dow Whiting', disclosed in U.S. Plant Pat. No. 20,883. Plants of the new *Chamaecyparis* differ from plants of 'Dow Whiting' in the following characteristics:

1. Plants of the new *Chamaecyparis* are larger than plants of 'Dow Whiting'.
2. Leaves of plants of the new *Chamaecyparis* are more green in color than and not as yellow as leaves of plants of 'Dow Whiting'.

BRIEF DESCRIPTION OF THE PHOTOGRAPH

The accompanying colored photograph illustrates the overall appearance of the new *Chamaecyparis* plant showing the colors as true as it is reasonably possible to obtain in colored reproductions of this type. Colors in the photograph may differ slightly from the color values cited in the detailed botanical description which accurately describe the colors of the new *Chamaecyparis* plant. The photograph is a side perspective view of a typical plant of 'SMNCLUTL' grown in an outdoor nursery.

DETAILED BOTANICAL DESCRIPTION

Plants used for the aforementioned photographs and following observations and measurements were grown during the summer in an outdoor nursery and three-gallon containers in Grand Haven, Mich. and under conditions which approximate commercial *Chamaecyparis* production. Plants were three years old when the photograph and description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Chamaecyparis lawsoniana* 'SMNCLUTL'.

Parentage:

*Female, or seed, parent.*—*Chamaecyparis lawsoniana* 'Sullivan', not patented.

*Male, or pollen, parent.*—Unknown proprietary selection of *Chamaecyparis lawsoniana*, not patented.

Propagation:

*Type.*—By softwood cuttings.

*Time to initiate roots, winter.*—About four months at temperatures about 10° C.

*Time to produce a rooted young plant, winter.*—About six months at temperatures about 13° C.

*Root description.*—Fine, fleshy; typically light brown in color, actual color of the roots is dependent on substrate composition, water quality, fertilizer, substrate temperature and physiological age of roots.

*Rooting habit.*—Moderate branching; medium density.

Plant description:

*Plant form and growth habit.*—Evergreen shrub; upright, arching and uniform plant habit; pyramidal in overall plant shape; vigorous growth habit and moderate growth rate.

*Branching habit.*—Freely branching with about 20 lateral branches per plant; dense and bushy plant form; plants maintain their lower branches and foliage at the soil level.

*Plant height.*—About 87 cm.

*Plant diameter.*—About 102 cm.

*Lateral branch description.*—Length: About 50 cm. Diameter: About 4 mm. Aspect: About 15° to 90° from vertical. Texture: Imbricate scales. Strength: Strong, flexible. Color, developing: Close to 174A. Color, developed: Close to 162A.

*Leaf description.*—Arrangement: Alternate. Length: About 2 mm. Width: About 0.5 mm. Shape: Thread-like. Apex: Apiculate. Base: Cuneate. Margin: Entire. Texture, upper and lower surface: Smooth, glabrous. Venation pattern: Parallel. Color: Developing leaves, upper and lower surfaces: Close to 143A. Fully expanded leaves, upper and lower surfaces: Close to 143A; venation, close to 143A; plants maintain their foliage color.

*Petioles.*—Length: About 2 mm. Diameter: About 2 mm. Color, upper and lower surfaces: Close to 143A.

*Cone description.*—To date, cone development has not been observed on plants of the new *Chamaecyparis*.

Pathogen & pest resistance: To date, plants of the new *Chamaecyparis* have not been noted to be resistant to pathogens or pests common to *Chamaecyparis* plants.

Garden performance: Plants of the new *Chamaecyparis* have been observed to be tolerant to drought, rain, wind and temperatures ranging from about −29° C. to about 36° C.

It is claimed:

1. A new and distinct *Chamaecyparis* plant named 'SMNCLUTL' as illustrated and described.

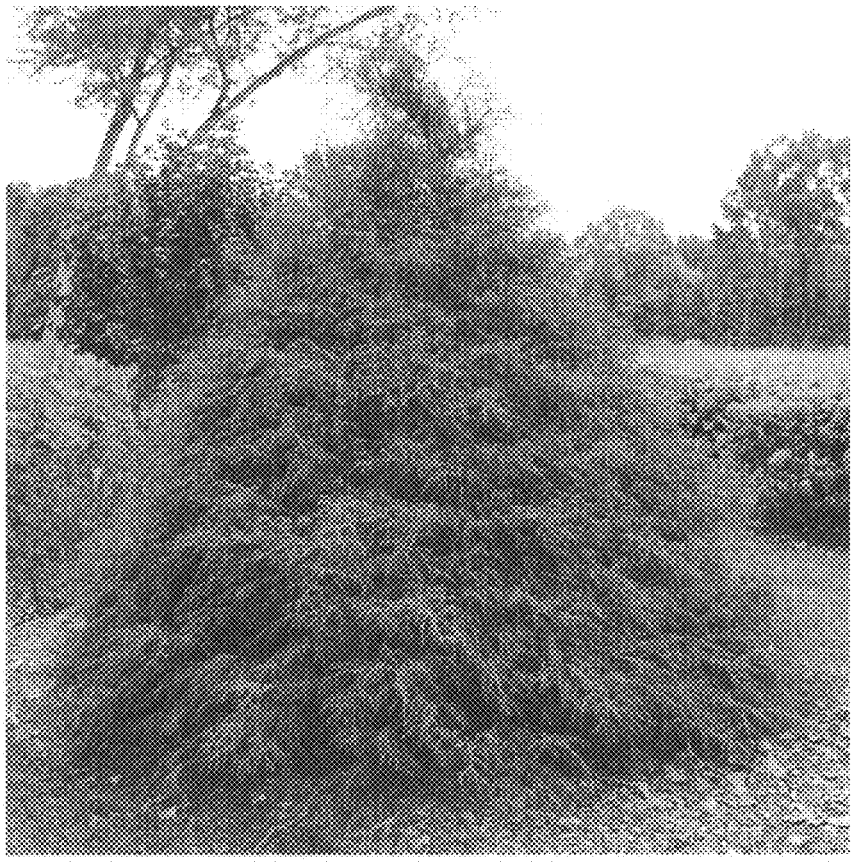

* * * * *